Figure 1:
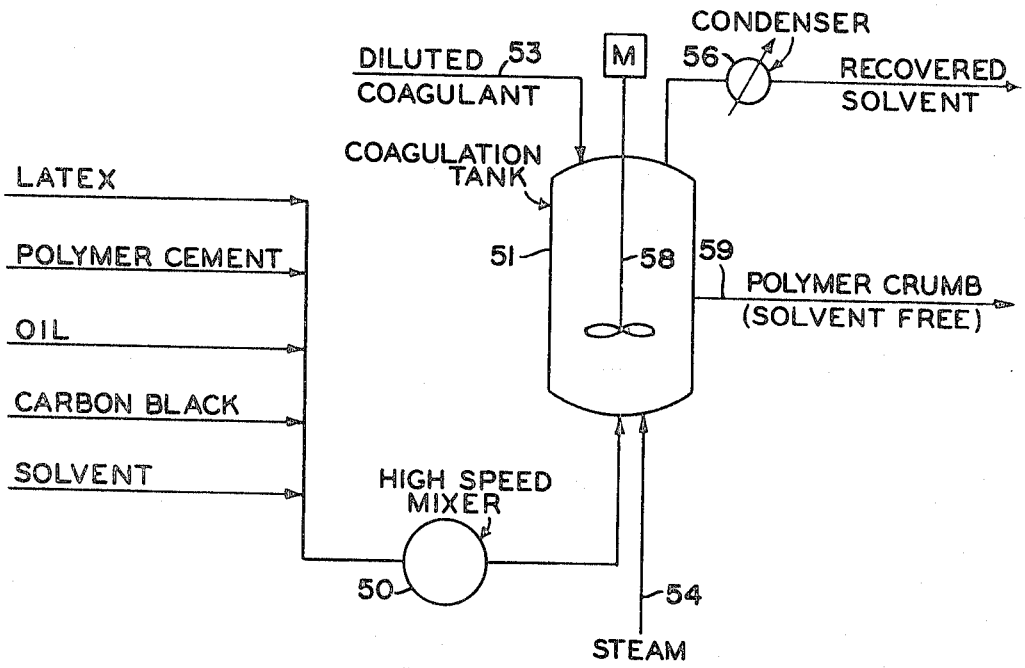
Figure 3:
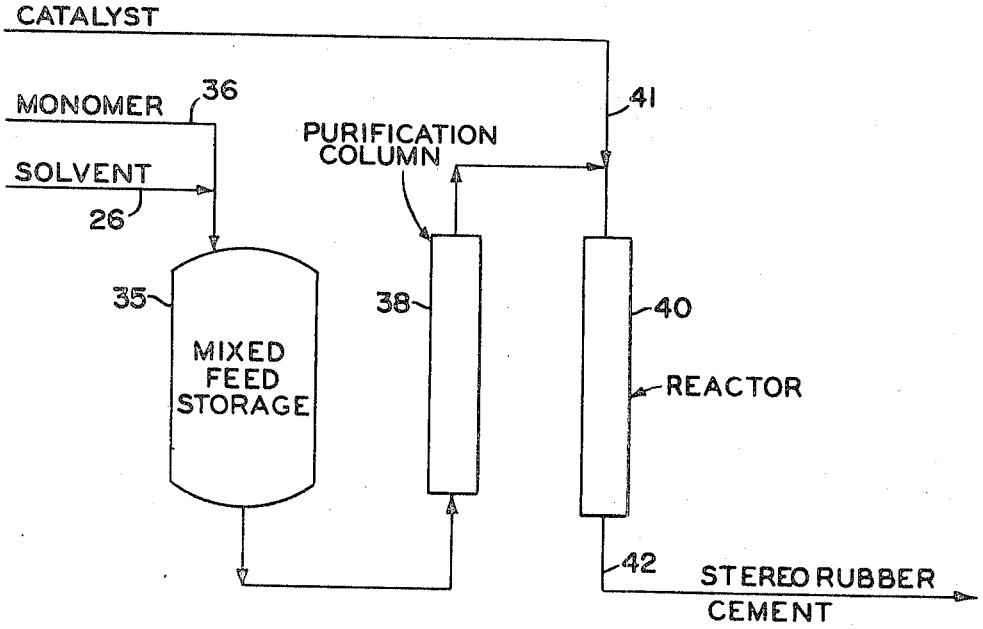
Figure 2:
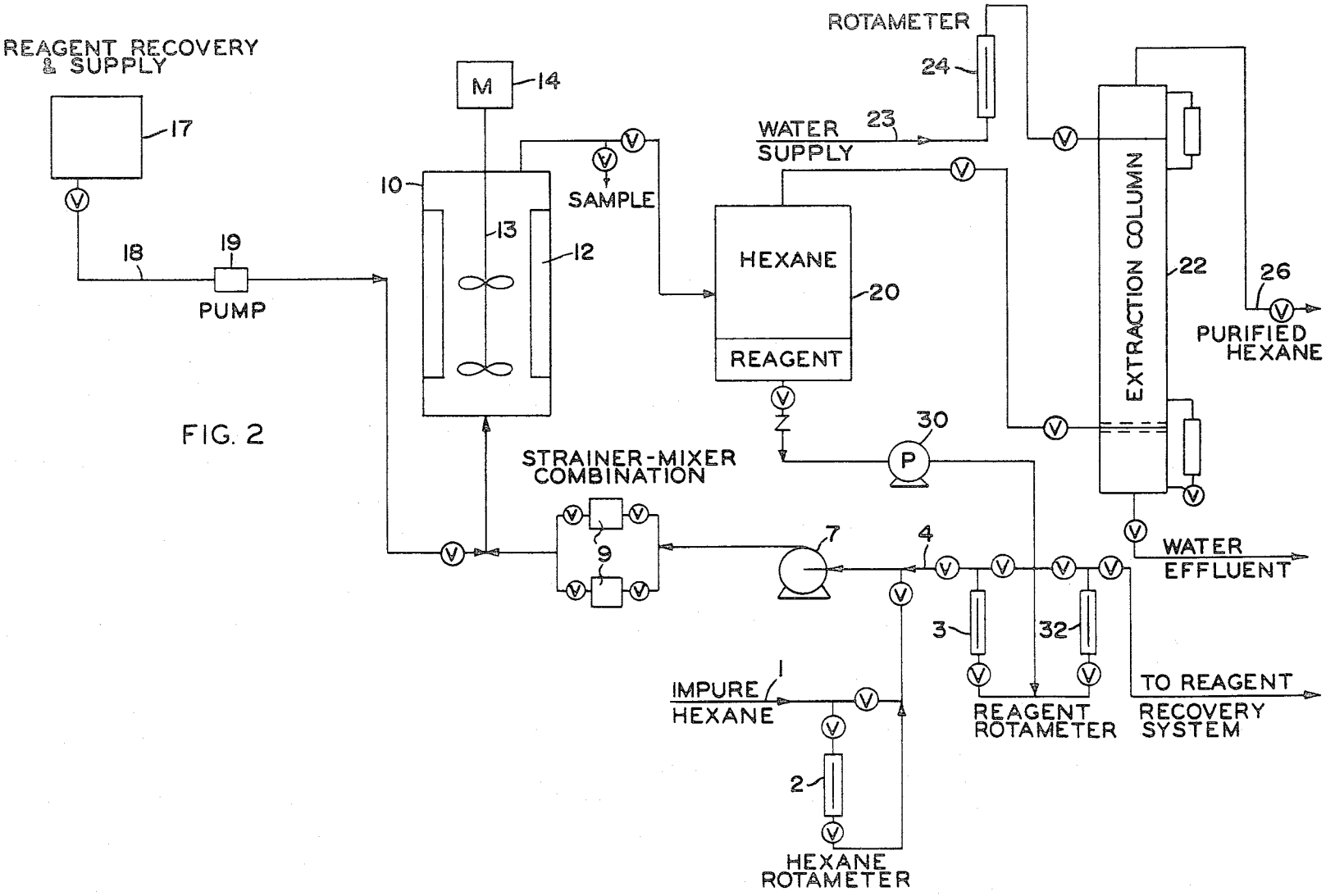

DEFENSIVE PUBLICATION

UNITED STATES PATENT OFFICE

Published at the request of the applicant or owner in accordance with the Notice of Dec. 16, 1969, 869 O.G. 687. The abstracts of Defensive Publication applications are identified by distinctly numbered series and are arranged chronologically. The heading of each abstract indicates the number of pages of specification, including claims and sheets of drawings contained in the application as originally filed. The files of these applications are available to the public for inspection and reproduction may be purchased for 30 cents a sheet.

Defensive Publication applications have not been examined as to the merits of alleged invention. The Patent Office makes no assertion as to the novelty of the disclosed subject matter.

PUBLISHED DECEMBER 14, 1971

893 O.G. 402

T893,005

PROCESS FOR REMOVING CARBON DISULFIDE FROM AN ORGANIC SOLVENT BY EMULSIFICATION EMPLOYING AN ALCOHOLIC ALKALI HYDROXIDE

Hossein Moosavian, Akron, Ohio, assignor to The Firestone Tire & Rubber Company, Akron, Ohio

Continuation of application Ser. No. 654,199, July 18, 1967. This application Oct. 26, 1970, Ser. No. 84,257

**Int. Cl. C07c *9/00***

U.S. Cl. 260—676

2 Sheets Drawing, 15 Pages Specification

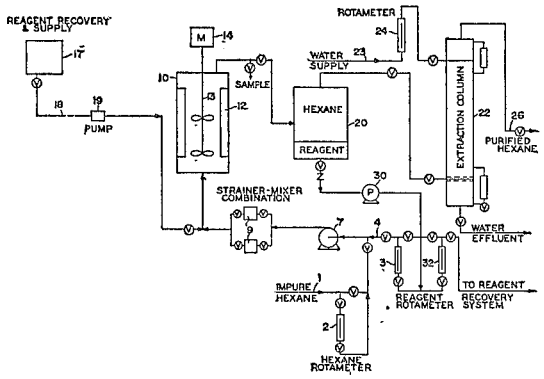

Hydrocarbon solvent recovered from a composite of (a) elastomer derived from a latex in which a dithiocarbamate has been used as a short-stopping agent, and (b) elastomer derived from a solution of the elastomer in said solvent, such as a rubber masterbatch which contains (1) carbon black, (2) oil, (3) elastomer derived from a latex in which a dithiocarbamate has been used as a short-stopping agent, and (4) elastomer derived from a solution of the elastomer in said solvent, is treated for removal of carbon disulfide generated from the dithiocarbamate. This is accomplished in a continuous process by first converting the carbon disulfide to water-soluble xanthate with a solution of a sodium or potassium hydroxide and methanol, and subsequently separating the xanthate from the solvent. The unreacted methanol-hydroxide reagent which is immiscible with the solvent separates from the solvent and on continued use becomes saturated with xanthate. Any further xanthate formed is carried with the solvent and is separated from it by washing with water, preferably by countercurrent extraction. The reagent is reused in the treatment of further solvent by recirculation, and its concentration is maintained by withdrawing some of the used reagent and adding some fresh reagent.

The reagent used is prepared by dissolving 10 or preferably 15 to 25 percent, and usually about 17 percent, of substantially anhydrous sodium or potassim hydroxide in 80 to 95 percent methanol. During the treatment of the solvent, water is formed, and after the operation has been functioning for several hours the reagent used contains about 15 to 30 percent of water. The solvent is usually hexane or other aliphatic hydrocarbon of 4 to 7 or 8 carbon atoms, but an organic solvent such as benzene or toluene may be employed.

BLACK MASTERBATCH SCHEMATIC FLOW DIAGRAM

SOLUTION POLYMERIZATION SCHEMATIC FLOW DIAGRAM